(12) United States Patent
Candau

(10) Patent No.: US 7,364,721 B2
(45) Date of Patent: *Apr. 29, 2008

(54) PHOTOSTABILIZATION OF DIBENZOYLMETHANE UV-SCREENING AGENTS WITH ARYLALKYL BENZOATE COMPOUNDS AND PHOTOPROTECTIVE COSMETIC COMPOSITIONS COMPRISED THEREOF

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 325 days.

This patent is subject to a terminal disclaimer.

(21) Appl. No.: 11/172,949

(22) Filed: Jul. 5, 2005

(65) Prior Publication Data

US 2006/0008430 A1 Jan. 12, 2006

Related U.S. Application Data

(60) Provisional application No. 60/588,984, filed on Jul. 20, 2004.

(30) Foreign Application Priority Data

Jul. 2, 2004 (FR) .................... 04 51416

(51) Int. Cl.
A61Q 17/04 (2006.01)
A61Q 17/00 (2006.01)
A61Q 19/04 (2006.01)
A61Q 19/00 (2006.01)
A61K 8/02 (2006.01)

(52) U.S. Cl. ............. 424/59; 60/400; 60/401
(58) Field of Classification Search .......... 424/59, 424/60, 400, 401
See application file for complete search history.

(56) References Cited

U.S. PATENT DOCUMENTS

| 5,849,273 | A | 12/1998 | Bonda et al. |
| 7,132,097 | B2 | 11/2006 | Bertz et al. |
| 2005/0152858 | A1 | 7/2005 | Bertz et al. |
| 2006/0067900 | A1 | 3/2006 | Bertz et al. |
| 2006/0067901 | A1 | 3/2006 | Bertz et al. |

FOREIGN PATENT DOCUMENTS

| FR | 2 800 991 A1 | 5/2001 |
| WO | WO 2005/009341 A2 | 2/2005 |
| WO | WO 2005/069822 A2 | 8/2005 |
| WO | WO 2005/117825 A1 | 12/2005 |
| WO | WO 2006/009828 A1 | 1/2006 |
| WO | WO 2006/041506 A2 | 4/2006 |

OTHER PUBLICATIONS

Japanese Official Action dated Jan. 30, 2007 comments and Notice of Reasons for Rejection.
XP002320817, "X-Tend™ 226, A Novel Ester with High Solubilizing Capacity", International Specialty Products, Aug. 2003.
French Search Report corresponding to FR 04/51416, issued on Mar. 14, 2005, 1 page.
English translation of French Search Report for FR 04/51416.

*Primary Examiner*—Shelley A. Dodson
(74) *Attorney, Agent, or Firm*—Buchanan, Ingersoll & Rooney, PC

(57) ABSTRACT

Topically applicable cosmetic/dermatological photoprotective compositions contain at least one dibenzoylmethane UV-screening agent, and, as a photostabilizer therefor, at least one arylalkyl benzoate compound of formula (I) or (II) below:

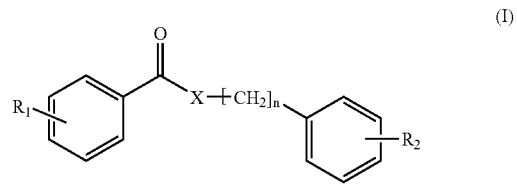

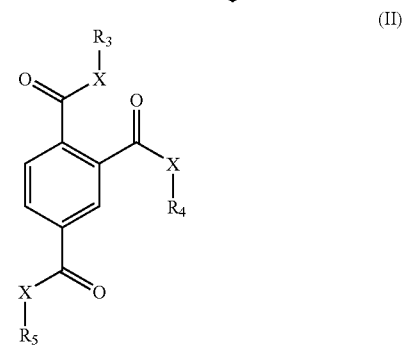

with the proviso that:
(i) the subject compositions are characteristically devoid of any octyl methoxycinnamate; and
(ii) same are other than a solution of butyl methoxydibenzoylmethane in 2-phenylethyl benzoate, 2-phenylethyl o-toluate, 2-phenylethyl p-toluate or in a 2-phenylethyl o-toluate/2-phenylethyl p-toluate (1/1) mixture.

18 Claims, No Drawings

PHOTOSTABILIZATION OF DIBENZOYLMETHANE UV-SCREENING AGENTS WITH ARYLALKYL BENZOATE COMPOUNDS AND PHOTOPROTECTIVE COSMETIC COMPOSITIONS COMPRISED THEREOF

CROSS-REFERENCE TO PRIORITY/PROVISIONAL APPLICATIONS

This application claims priority under 35 U S.C § 119 (a)-(d) of FR 04/51416, filed Jul. 2, 2004, and claims benefit under 35 U.S.C. § 119(e) of provisional application No. 60/588,984, filed Jul. 20, 2004, each hereby expressly incorporated by reference and each assigned to the assignee hereof.

CROSS-REFERENCE TO COMPANION APPLICATIONS

Copending applications Ser. Nos. 11/172,932 and 11/172,902, each filed concurrently herewith and each also assigned to the assignee hereof.

BACKGROUND OF THE INVENTION

1. Technical Field of the Invention

The present invention relates to a process for photostabilizing, with respect to UV radiation, at least one dibenzoylmethane UV-screening agent with at least one arylalkyl benzoate compound.

The present invention also relates to novel photoprotective compositions, in particular cosmetic compositions for topical application.

2. Description of Background and/or Related and/or Prior Art

It is known that light radiation with wavelengths of from 280 nm to 400 nm allows tanning of the human epidermis and that light rays more particularly ranging from 280 to 320 nm, known as UV-B rays, cause skin burns and erythema which can harm the development of a natural tan. For these reasons, as well as for aesthetic reasons, there is a constant demand for means of controlling this natural tanning so as to thus control the color of the skin; this UV-B radiation should thus be screened out.

It is also known that UV-A rays, with wavelengths of from 320 to 400 nm, which cause tanning of the skin, are liable to induce adverse changes therein, in particular in the case of sensitive skin or skin which is continually exposed to solar radiation. UV-A rays cause in particular a loss of elasticity of the skin and the appearance of wrinkles leading to premature aging of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A rays on their skin. It is therefore desirable to also screen out the UV-A radiation.

For the purpose of protecting the skin and keratin materials against UV radiation, anti-sun/sunscreen compositions comprising organic screening agents that are active in the UV-A range and in the UV-B range are generally used. The majority of these screening agents are liposoluble.

In this respect, a particularly advantageous family of UV-A screening agents currently consists of dibenzoylmethane derivatives, and in particular 4-tert-butyl-4'-methoxydibenzoylmethane, which are liposoluble and in fact have a high intrinsic absorbing power. These dibenzoylmethane derivatives, which are products that are now well known per se as screening agents that are active in the UV-A range, are described in particular in FR-A-2,326,405 and FR-A-2,440,933, and also in EP-A-0,114,607; 4-tert-butyl-4'-methoxydibenzoylmethane is, moreover, currently marketed under the trademark "Parsol 1789" by Roche Vitamins.

Unfortunately, it has been found that dibenzoylmethane derivatives are products that are relatively sensitive to ultraviolet radiation (especially UV-A), i.e., more specifically, they have an annoying tendency to be degraded more or less rapidly under the action of this UV. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and frequent time intervals in order to obtain effective protection of the skin against UV rays.

Dibenzoylmethane derivatives are oil-soluble solid screening agents. Among the oils capable of effectively solubilizing these UV-screening agents, alcohol benzoates are known, in particular C12/C1-5 alkyl benzoates, for instance the commercial products Finsolv TN or Witconol APM manufactured and marketed by Witco.

However, the alcohol benzoates known to date do not make it possible to solve the problem of the photostability of dibenzoylmethane derivatives with respect to UV radiation.

WO 2005/009341 discloses screening compositions based on organic screening agents in which an aryl phenylethyl ester compound is used as a solvent for the screening agents in oils. That document teaches that this type of compound makes it possible to effectively solubilize the dibenzoylmethane derivative: butyl methoxydibenzoylmethane. It describes solutions of butyl methoxydibenzoylmethanes in 2-phenylethyl benzoate, 2-phenylethyl o-toluate, 2-phenylethyl p-toluate or in a 2-phenylethyl o-toluate/2-phenylethyl p-toluate (1/1) mixture. It also describes anti-sun compositions containing butyl methoxydibenzoylmethane in the presence of octyl methoxycinnamate. That document does not, however, mention the problem of the photoinstability of dibenzoylmethane derivatives.

SUMMARY OF THE INVENTION

It has now surprisingly been determined that by combining the dibenzoylmethane sunscreens mentioned above with an effective amount of a particular alcohol benzoate of the arylalkyl benzoate compound type, it is possible to substantially and notably improve the photochemical stability (or photostability) of these same dibenzoylmethane sunscreens.

This essential discovery forms the basis of the present invention.

Thus, the present invention features a process for improving the stability of at least one dibenzoylmethane UV-screening agent with respect to UV radiation, which comprises combining said dibenzoylmethane sunscreen with at least one arylalkyl benzoate compound of formula (I) or (II) as defined above.

The present invention also features cosmetic or dermatological compositions for topical application which comprise, in a cosmetically acceptable carrier:

(a) at least one UV-screening agent of the dibenzoylmethane derivative type and (b) at least one arylalkyl benzoate compound of formula (I) or (II); with the proviso that:

(i) said composition does not contain any octyl methoxycinnamate;

(ii) said composition is different from a solution of butyl methoxydibenzoylmethane in 2-phenylethyl benzoate, 2-phenylethyl o-toluate, 2-phenylethyl p-toluate or in a 2-phenylethyl o-toluate/2-phenylethyl p-toluate (1/1) mixture.

Specifically, the presence of octyl methoxycinnamate in a composition comprising the combination of a dibenzoylmethane sunscreen and an arylalkyl benzoate compound can result in considerable destabilization, with respect to UV radiation, of the composition, that results in substantial degradation of the dibenzoylmethane UV-screening agent.

Finally, the present invention also features formulating an arylalkyl benzoate compound in a cosmetic or dermatological composition comprising at least one dibenzoylmethane sunscreen, for the purpose of improving the stability with respect to UV rays of said dibenzoylmethane sunscreen.

Other characteristics, aspects and advantages of the invention will become apparent from the detailed description that follows.

DETAILED DESCRIPTION OF BEST MODE AND SPECIFIC/PREFERRED EMBODIMENTS OF THE INVENTION

Among the dibenzoylmethane sunscreens according to the invention, particularly representative are:

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4'-tert-butyl-4'-methoxydibenzoylmethane.

Among the dibenzoylmethane sunscreens mentioned above, use will in particular be made of 4-isopropyldibenzoylmethane, marketed under the name "Eusolex 8020" by Merck, and corresponding to the following formula:

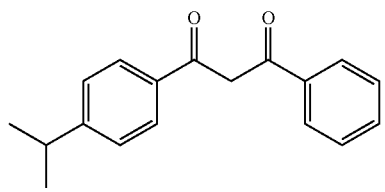

It is most particularly preferred to use 4-(tert-butyl)-4'-methoxydibenzoylmethane or butyl methoxydibenzoylmethane, marketed under the trademark "Parsol 1789" by Roche Vitamins; this screening agent corresponds to the following formula:

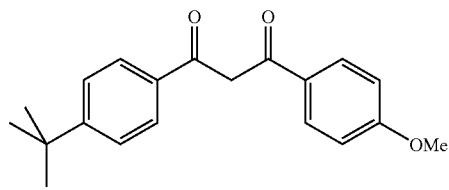

The dibenzoylmethane derivative(s) may be present in the compositions in accordance with the invention in amounts that preferably range from 0.01 to 10% by weight, and more preferably from 0.1 to 6% by weight, relative to the total weight of the composition.

The arylalkyl benzoate compounds in accordance with the invention are preferably selected from among those of formula (I) or (II) below:

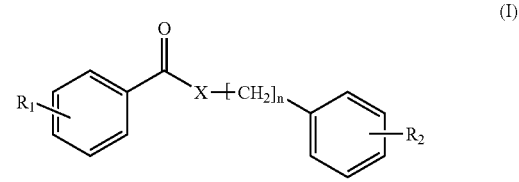

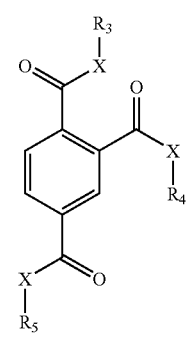

in which:

X is O, S or N;

n is an integer ranging from 1 to 10, and more preferably from 2 to 6;

$R_1$ is a hydrogen atom, a halogen atom, a linear or branched $C_1$-$C_4$ alkoxy radical (preferably methoxy or ethoxy), a nitro radical, an amino radical, or a $C_6H_6SO_2$ radical;

$R_2$ is a hydrogen atom, a hydroxyl group, a halogen atom, a linear or branched $C_1$-$C_4$ alkoxy radical (preferably methoxy or ethoxy), a nitro radical, an amino radical, or a $C_6H_6SO_2$ radical;

$R_3$, $R_4$ and $R_5$, which may be identical or different, are each a radical of formula:

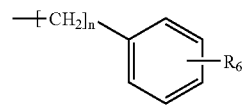

in which n has the same definition indicated above; and $R_6$ is a hydrogen atom, a hydroxyl group, a linear or branched $C_1$-$C_4$ alkoxy radical (preferably methoxy or ethoxy), a nitro radical, an amino radical, or a $C_6H_6SO_2$ radical.

The arylalkyl benzoate compounds in accordance with the invention and the syntheses thereof have long been known in the chemistry literature, and in particular in PL 55230.

Among the arylalkyl benzoate compounds mentioned above, use will more particularly be made of 2-ethyl phenyl benzoate

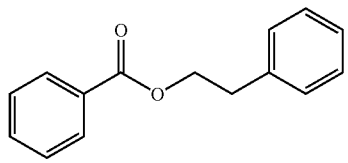

for instance the commercial product X-Tend 226® marketed by ISP.

According to the present invention, the arylalkyl benzoate compound(s) will be used in a sufficient amount for obtaining a notable and significant improvement in the photostability of the dibenzoylmethane derivative in a given composition. This minimum amount of photostabilizing agent to be used can vary according to the amount of dibenzoylmethane present at the start in the composition and according to the nature of the cosmetically acceptable carrier selected for the composition. It can be determined without difficulty by means of a conventional test for measuring photostability.

The arylalkyl benzoate compounds in accordance with the invention may be present in the compositions in accordance with the invention in amounts ranging from 0.1 to 40% by weight, and more preferably from 0.1 to 30% by weight, relative to the total weight of the composition.

The compositions in accordance with the invention may also comprise other additional organic or inorganic photoprotective agents that are active in the UV-A range and/or UV-B range, and that are water-soluble or liposoluble or alternatively insoluble in the cosmetic solvents commonly used.

The additional organic photoprotective agents are in particular selected from among anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzoazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303, 549, DE-197,26,184 and EP-893,119; benzoxazole derivatives as described in EP-0,832,642, EP-1,027,883, EP-1, 300,137 and DE-101,62,844; screening polymers and screening silicones such as those described in particular in WO 93/04665; dimers derived from α-alkylstyrene, such as those described in DE-198,55,649; 4,4-diarylbutadienes as described in EP-0,967,200, DE-197,46,654, DE-197,55,649, EP-A-1,008,586, EP-1,133,980 and EP-133,981, and mixtures thereof.

As examples of additional organic photoprotective agents, mention may be made of those denoted hereinbelow under their INCI name:

Para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.
Salicylic Derivatives:
Homosalate marketed under the name "Eusolex HMS" by Rona/EM Industries,
Ethylhexyl salicylate marketed under the name "Neo Heliopan OS" by Haarmann and Reimer,
Dipropylene glycol salicylate marketed under the name "Dipsal" by Scher, TEA salicylate, marketed under the name "Neo Heliopan TS" by Haarmann and Reimer.
β,β-diphenylacrylate Derivatives:
Octocrylene marketed in particular under the trademark "Uvinul N539" by BASF,
Etocrylene marketed in particular under the trademark "Uvinul N35" by BASF.
Benzophenone Derivatives:
Benzophenone-1 marketed under the trademark "Uvinol 400" by BASF,
Benzophenone-2 marketed under the trademark "Uvinol D50" by BASF,
Benzophenone-3 or oxybenzone, marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "SpectraSorb UV-24" by American Cyanamid,
Benzophenone-9 marketed under the trademark "Uvinul DS-49" by BASF,
Benzophenone-12,
n-Hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Phenylbenzimidazole Derivatives:
Phenylbenzimidazolesulfonic acid marketed in particular under the trademark "Eusolex 232" by Merck,
Disodium phenyl dibenzimidazole tetrasulfonate marketed under the trademark "Neo Heliopan AP" by Haarmann and Reimer.
Phenylbenzotriazole Derivatives:
Drometrizole trisiloxane marketed under the name "Silatrizole" by Rhodia Chimie,
Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.
Triazine Derivatives:
Ethylhexyl triazone marketed in particular under the trademark "Uvinul T150" by BASF, Diethylhexyl butamido triazone marketed under the trademark "Uvasorb HEB" by Sigma 3V,
2,4,6-tris(diisobutyl 4'-aminobenzalmalonate)-s-triazine.
Anthranilic Derivatives:
Menthyl anthranilate marketed under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxanes containing benzalmalonate functions, for instance Polysilicone-15 marketed under the trademark "Parsol SLX" by Hoffmann LaRoche.
4,4-diarylbutadiene Derivatives:
1,1-dicarboxy(2,2'-dimethylpropyl)-4,4-diphenylbutadiene.
Benzoxazole Derivatives:
2,4-bis[5-(1-dimethylpropyl)benzoxazol-2-yl-(4-phenyl) imino]-6-(2-ethylhexyl)imino-1,3,5-triazine marketed under the name Uvasorb K2A by Sigma 3V, and mixtures thereof.

The preferred additional organic photoprotective agents are selected from among:
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyl dibenzimidazole tetrasulfonate,
Methylenebis(benzotriazolyl)tetramethylbutylphenol,
Ethylhexyl triazone,
Diethylhexyl butamido triazone,
Drometrizole trisiloxane,
Polysilicone-15,
1,1-Dicarboxy(2,2'-dimethylpropyl)-4,4-diphenylbutadiene,
2,4-bis[5-(1-Dimethylpropyl)benzoxazol-2-yl-(4-phenyl) imino]-6-(2-ethylhexyl)imino-1,3,5-triazine, and mixtures thereof.

The additional inorganic photoprotective agents are selected from among pigments, and even more preferably nanopigments (mean size of the primary particles: generally from 5 nm to 100 nm, preferably from 10 nm to 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen or elastin), alkanolamines, silicon oxides, metal oxides, sodium hexametaphosphate, alumina or glycerol.

The treated nanopigments may more particularly be titanium oxides treated with:
  silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide,
  alumina and aluminum stearate, such as the product "Microtitanium Dioxide MT 100 T" from the company Tayca,
  alumina and aluminum laurate, such as the product "Microtitanium Dioxide MT 100 S" from the company Tayca,
  iron oxides and iron stearate, such as the product "Microtitanium Dioxide MT 100 F" from the company Tayca,
  silica, alumina and silicone, such as the products "Microtitanium Dioxide MT 100 SAS", "Microtitanium Dioxide MT 600 SAS" and "Microtitanium Dioxide MT 500 SAS" from the company Tayca,
  sodium hexametaphosphate, such as the product "Microtitanium Dioxide MT 150 W" from the company Tayca,
  octyltrimethoxysilane, such as the product "T-805" from the company Degussa,
  alumina and stearic acid, such as the product "UVT-M160" marketed by Kemira,
  alumina and glycerol, such as the product "UVT-M212" from the company Kemira,
  alumina and silicone, such as the product "UVT-M262" from the company Kemira.

Other titanium oxide nanopigments treated with a silicone are preferably $TiO_2$ treated with octyltrimethylsilane and for which the mean size of the elementary particles is from 25 to 40 nm, such as the product marketed under the trademark "T 805" by Degussa Silices, $TiO_2$ treated with a polydimethylsiloxane and for which the mean size of the elementary particles is 21 nm, such as the product marketed under the trademark "70250 Cardre UF TiO2SI3" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Color Techniques.

The uncoated titanium oxide nanopigments are marketed, for example, by Tayca under the trademarks "Microtitanium Dioxide MT 500 B" or "Microtitanium Dioxide MT600 B", by Degussa under the name "P 25", by Wackher under the name "Transparent titanium oxide PW", by Miyoshi Kasei under the name "UFTR", by Tomen under the name "ITS" and by Tioxide under the name "Tioveil AQ".

The uncoated zinc oxide nanopigments are, for example:
  those marketed under the name "Z-Cote" by Sunsmart;
  those marketed under the name "Nanox" by Elementis;
  those marketed under the name "Nanogard WCD 2025" by Nanophase Technologies.

The coated zinc oxide nanopigments are, for example:
  those marketed under the name "Zinc Oxide CS-5" by Toshibi (ZnO coated with polymethylhydrogenosiloxane);
  those marketed under the name "Nanogard Zinc Oxide FN" by Nanophase Technologies (as a 40% dispersion in Finsolv TN, $C_{12}$-$C_{15}$ alcohol benzoate);
  those marketed under the name "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);
  those marketed under the name "NFD Ultrafine ZNO" by Daikin (ZnO coated with perfluoroalkyl phosphate and copolymer based on perfluoroalkylethyl as a dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "Escalol Z100" by ISP (alumina-treated ZnO dispersed in an ethylhexyl methoxycinnamate/PVP-hexadecene/methicone copolymer mixture);

those marketed under the name "Fuji ZNO-SMS-10" by Fuji Pigment (ZnO coated with silica and polymethylsilsesquioxane);

those marketed under the name "Nanox Gel TN" by Elementis (ZnO dispersed at a concentration of 55% in $C_{12}$-$C_{15}$ alcohol benzoate with hydroxystearic acid polycondensate).

The uncoated cerium oxide nanopigments are marketed under the name "Colloidal Cerium Oxide" by Rhône Poulenc.

The uncoated iron oxide nanopigments are marketed, for example, by Arnaud under the names "Nanogard WCD 2002 (FE 45B)", "Nanogard Iron FE 45 BL AQ", "Nanogard FE 45R AQ", "Nanogard WCD 2006 (FE 45R)", or by Mitsubishi under the name "TY-220".

The coated iron oxide nanopigments are marketed, for example, by Arnaud under the names "Nanogard WCD 2008 (FE 45B FN)", "Nanogard WCD 2009 (FE 45B 556)", "Nanogard FE 45 BL 345", "Nanogard FE 45 BL", or by BASF under the name "Transparent Iron Oxide".

Mention may also be made of mixtures of metal oxides, in particular of titanium dioxide and of cerium dioxide, including the equal-weight mixture of titanium dioxide and of cerium dioxide coated with silica, marketed by Ikeda under the name "Sunveil A", and also the mixture of titanium dioxide and of zinc dioxide coated with alumina, silica and silicone, such as the product "M 261" marketed by Kemira, or coated with alumina, silica and glycerol, such as the product "M 211" marketed by Kemira.

The nanopigments may be introduced into the compositions according to the invention in unmodified form or in the form of a pigmentary paste, i.e., as a mixture with a dispersing agent, as described, for example, in GB-A-2,206,339.

The additional photoprotective agents are generally present in the compositions according to the invention in proportions ranging from 0.01 to 20% by weight relative to the total weight of the composition, and preferably ranging from 0.1 to 10% by weight relative to the total weight of the composition.

The compositions according to the invention may also contain agents for artificially tanning and/or browning the skin (self-tanning agents), and more particularly dihydroxyacetone (DHA). They are preferably present in amounts ranging from 0.1 to 10% by weight relative to the total weight of the composition.

The compositions in accordance with the present invention may also comprise standard cosmetic adjuvants, in particular selected from fatty substances, organic solvents, ionic or nonionic, hydrophilic or lipophilic thickeners, softeners, humectants, opacifiers, stabilizers, emollients, silicones, antifoaming agents, fragrances, preservatives, anionic, cationic, nonionic, zwitterionic or amphoteric surfactants, active agents, fillers, polymers, propellants, acidifying or basifying agents or any other ingredient normally used in the cosmetics and/or dermatological field.

The fatty substances may consist of an oil or a wax or mixtures thereof. The term "oil" means a compound that is liquid at ambient temperature. The term "wax" means a compound that is solid or substantially solid at ambient temperature and whose melting point is generally greater than 35° C.

Oils that may be mentioned include mineral oils (paraffin); plant oils (sweet almond oil, macadamia oil, blackcurrant seed oil, jojoba oil); synthetic oils, such as perhydrosqualene, fatty alcohols, fatty acids or fatty esters (such as the $C_{12}$-$C_{15}$ alcohol benzoate marketed under the trademark "Finsolv TN" or "Witconol TN" by Witco, octyl palmitate, isopropyl lanolate and triglycerides, including capric/caprylic acid triglycerides), oxyethylenated or oxypropylenated fatty esters and ethers; silicone oils (cyclomethicone, polydimethylsiloxanes, or PDMS) or fluoro oils, and polyalkylenes.

Waxy compounds that may be mentioned include paraffin, carnauba wax, beeswax and hydrogenated castor oil.

Among the organic solvents, mention may be made of lower alcohols and polyols. These polyols may be selected from glycols and glycol ethers, such as ethylene glycol, propylene glycol, butylene glycol, dipropylene glycol or diethylene glycol.

Hydrophilic thickeners that may be mentioned include carboxyvinyl polymers such as the carbopol products (carbomers) and the Pemulen products (acrylate/C10-C30-alkyl acrylate copolymer); polyacrylamides, for instance the crosslinked copolymers marketed under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by Seppic; 2-acrylamido-2-methylpropanesulfonic acid polymers and copolymers, optionally crosslinked and/or neutralized, such as the poly(2-acrylamido-2-methylpropanesulfonic acid) marketed by Hoechst under the trademark "Hostacerin AMPS" (CTFA name: ammonium polyacryldimethyltauramide); cellulose-based derivatives such as hydroxyethylcellulose; polysaccharides and in particular gums such as xanthan gum; and mixtures thereof.

Lipophilic thickeners that may be mentioned include modified clays such as hectorite and its derivatives, for instance the products marketed under the name Bentone.

Among the active agents, representative are:
antipollution agents and/or free-radical scavengers;
depigmenting agents and/or pro-pigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellents;
substance P or CRGP antagonists.

Of course, one skilled in this art will take care to select the optional additional compound(s) mentioned above and/or the amounts thereof such that the advantageous properties intrinsically associated with the compounds in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type. They may in particular be in the form of a simple or complex emulsion (O/W, W/O, O/W/O or W/O/W) such as a cream or a milk, in the form of a gel or of a cream-gel, in the form of a lotion, a powder or a solid tube, and may optionally be packaged as an aerosol and may be in the form of a mousse or a spray.

The compositions according to the invention are preferably in the form of an oil-in-water or water-in-oil emulsion.

The emulsions generally contain at least one emulsifier selected from amphoteric, anionic, cationic and nonionic emulsifiers, which are used alone or as a mixture. The emulsifiers are appropriately selected according to the emulsion to be obtained (W/O or O/W).

As emulsifying surfactants that can be used for preparing the W/O emulsions, mention may be made, for example, of alkyl esters or ethers of sorbitan, of glycerol or of sugars; silicone surfactants, for instance dimethicone copolyols, such as the mixture of cyclomethicone and of dimethicone copolyol, marketed under the name "DC 5225 C" by Dow Corning, and alkyldimethicone copolyols such as the laurylmethicone copolyol marketed under the name "Dow Corning 5200 Formulation Aid" by Dow Corning; cetyl dimethicone copolyol, such as the product marketed under the name Abil EM 90R by Goldschmidt, and the mixture of cetyl dimethicone copolyol, of polyglyceryl isostearate (4 mol) and of hexyl laurate, marketed under the name Abil WE 09 by Goldschmidt. One or more co-emulsifiers may also be added thereto, which may be selected advantageously from the group comprising polyol alkyl esters. Polyol alkyl esters that may in particular be mentioned include glycerol and/or sorbitan esters, for example polyglyceryl isostearate, such as the product marketed under the name Isolan GI 34 by Goldschmidt, sorbitan isostearate, such as the product marketed under the name Arlacel 987 by ICI, sorbitan glyceryl isostearate, such as the product marketed under the name Arlacel 986 by ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, in particular alkyl polyglucosides (APGs) such as decyl glucoside and lauryl glucoside marketed, for example, by Henkel under the respective names Plantaren 2000 and Plantaren 1200, cetostearyl glucoside optionally as a mixture with cetostearyl alcohol, marketed, for example, under the name Montanov 68 by Seppic, under the name Tegocare CG90 by Goldschmidt and under the name Emulgade KE3302 by Henkel, and also arachidyl glucoside, for example in the form of a mixture of arachidyl alcohol, behenyl alcohol and arachidyl glucoside, marketed under the name Montanov 202 by Seppic. According to a particular embodiment of the invention, the mixture of alkyl polyglucoside as defined above with the corresponding fatty alcohol may be in the form of a self-emulsifying composition as described, for example, in document WO-A-92/06778.

When an emulsion is involved, the aqueous phase of this emulsion may comprise a nonionic vesicular dispersion prepared according to known processes (Bangham, Standish and Watkins. *J. Mol. Biol.*, 13, 238 (1965), FR-2,315,991 and FR-2,416,008).

The compositions according to the invention find their application in a large number of treatments (regime or regimen), especially cosmetic treatments, of the skin, the lips and the hair, including the scalp, in particular for protecting and/or caring for the skin, the lips and/or the hair, and/or for making up the skin and/or the lips.

The present invention also features the use of the subject compositions as defined above, for producing products for the cosmetic treatment of the skin, the lips, the nails, the hair, the eyelashes, the eyebrows and/or the scalp, in particular care products and makeup products.

The cosmetic compositions according to the invention may, for example, be used as care products and/or anti-sun products for the face and/or the body, of liquid or semi-liquid consistency, such as milks, more or less rich creams, cream-gels and pastes. They may optionally be packaged as an aerosol and may be in the form of a mousse or of a spray.

The compositions according to the invention in the form of vaporizable fluid lotions in accordance with the invention are applied to the skin or the hair in the form of fine particles by means of pressurization devices. The devices in accordance with the invention are well known to those skilled in the art and include non-aerosol pumps or "atomizers", aerosol containers comprising a propellant and also aerosol pumps that use compressed air as propellant. The latter are described in U.S. Pat. Nos. 4,077,411 and 4,850,517 (forming an integral part of the content of the description).

The compositions packaged in the form of an aerosol in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES 1 to 3

The following three (3) specific anti-sun formulations were prepared; the amounts are indicated in percentages by weight:

| Compositions | Example 1 (not the invention) | Example 2 (invention) | Example 3 (invention) |
|---|---|---|---|
| PHASE A | | | |
| Polydimethylsiloxane | 0.5 | 0.5 | 0.5 |
| Preservatives | 1.0 | 1.0 | 1.0 |
| Stearic acid | 1.5 | 1.5 | 1.5 |
| Glyceryl monostearate/ PEG stearate mixture (100 EO) | 1.0 | 1.0 | 1.0 |
| Cetylstearyl glucoside/ cetylstearyl alcohol mixture | 2.0 | 2.0 | 2.0 |
| Cetyl acid | 0.5 | 0.5 | 0.5 |
| Butyl methoxydibenzoyl-methane (Parsol 1789 - Roche Vitamins) | 2.0 | 2.0 | 2.0 |
| 2-Phenylethyl benzoate (X-Tend 226 from ISP) | — | 5 | 10 |
| C12/C15 alcohol benzoate (Finsolv TN - Witco) | 10 | 5 | — |

-continued

| Compositions | Example 1 (not the invention) | Example 2 (invention) | Example 3 (invention) |
|---|---|---|---|
| PHASE B | | | |
| Glycerol | 5.0 | 5.0 | 5.0 |
| Xanthan gum | 0.2 | 0.2 | 0.2 |
| Cetyl phosphate | 1.0 | 1.0 | 1.0 |
| Sequestering agent | 0.1 | 0.1 | 0.1 |
| Deionized water | qs 100 | qs 100 | qs 100 |
| PHASE C | | | |
| Isohexadecane | 1.0 | 1.0 | 1.0 |
| Acrylic acid/stearyl methacrylate copolymer | 0.2 | 0.2 | 0.2 |
| Triethanolamine | qs | qs | qs |

Procedure for Preparing the Formulation Examples 1 to 3:

The aqueous phase (Phase B) containing all of its ingredients is heated to 80° C. in a water bath. The fatty phase (Phase A) containing all of its ingredients is heated to 80° C. in a water bath. A is emulsified in B with stirring of rotor-stator type (device from the company Moritz). Phase C is incorporated and the mixture is allowed to return to ambient temperature with moderate stirring. The triethanolamine is introduced so as to adjust the pH to the desired value at the end of the production.

Dibenzoylmethane Photostability Test:

For each of these compositions, the percentage of residual 4-tert-butyl-4'-methoxydibenzoylmethane after UV irradiation is determined according to the following protocol:

For each formula, 3 test samples and 3 control samples were prepared. 2 mg/cm² of formula were deposited, with a spatula, onto poly(methyl methacrylate) plates. The test plates were exposed for 43 min to the Heraeus Suntest equipped with a Xenon lamp having a UV-A flux of: $8.34 \times 10^{-3}$ W/cm² and a UV-B flux of: $0.471 \times 10^{-4}$ W/cm² and the control plates were kept in the dark for the same amount of time and at the same temperature (38-40° C.).

At the end of this period of time, the screening agents were extracted by immersing each plate in 50 g of methanol and subjecting them to ultrasound for 15 min in order to ensure good extraction. The solutions obtained were analyzed by high performance liquid chromatography.

For each formula tested, the amount of residual dibenzoylmethane after exposure is given by the ratio of its concentration in the sample exposed to its concentration in the sample not exposed. The results obtained are given in the table below:

TABLE 1

| Composition | Residual fraction of dibenzoylmethane after irradiation (% by weight) |
|---|---|
| Example 1 (not the invention) | 25 ± 4 |
| Example 2 (invention) | 37 ± 3 |
| Example 3 (invention) | 69.5 ± 6 |

It is observed that, in formulations 2 and 3 containing butyl methoxydibenzoylmethane combined with an arylalkyl benzoate compound, the photostability of the dibenzoylmethane is substantially improved compared with formulation 1 having an identical carrier containing butyl methoxydibenzoylmethane at the same concentration in the presence of a $C_{12}$-$C_{15}$ alkyl benzoate.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostable cosmetic/dermatological photoprotective composition, comprising an effective UV-photoprotecting amount of at least one dibenzoylmethane UV-screening agent, and, as a photostabilizer therefor, a thus effective amount of at least one arylalkyl benzoate compound of formula (I) or (II) below:

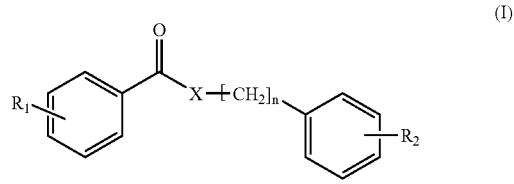

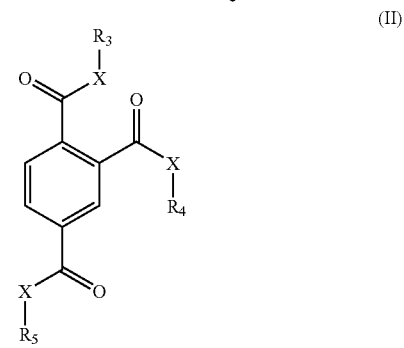

in which:

X is O, S or N;

n is an integer ranging from 1 to 10;

$R_1$ is a hydrogen atom, a halogen atom, a linear or branched $C_1$-$C_4$ alkoxy radical, a nitro radical, an amino radical, or a $C_6H_6SO_2$ radical;

$R_2$ is a hydrogen atom, a hydroxyl group, a halogen atom, a linear or branched $C_1$-$C_4$ alkoxy radical, a nitro radical, an amino radical, or a $C_6H_6SO_2$ radical;

$R_3$, $R_4$ and $R_5$, which may be identical or different, are each a radical of formula:

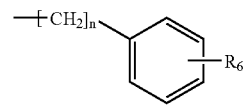

in which n is as defined above; and $R_6$ is a hydrogen atom, a hydroxyl group, a linear or branched $C_1$-$C_4$ alkoxy radical, a nitro radical, an amino radical, or a $C_6H_6SO_2$ radical, formulated into a topically applicable cosmetically/dermatologically acceptable medium.

2. The cosmetic/dermatological composition as defined by claim 1, said at least one dibenzoylmethane UV-screening agent being selected from the group consisting of:
2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylrnethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane, and
2,6-dimethyl-4'-tert-butyl-4'-methoxydibenzoylmethane.

3. The cosmetic/dermatological composition as defined by claim 1, said at least one dibenzoylmethane UV-screening agent comprising 4-(tert-butyl)-4'-methoxydibenzoylmethane or butyl methoxydibenzoylmethane.

4. The cosmetic/dermatological composition as defined by claim 1, said at least one arylalkyl benzoate compound comprising 2-phenylethyl benzoate of formula:

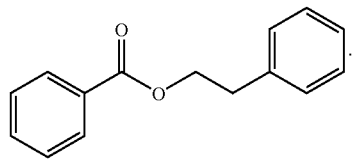

5. The cosmetic/dermatological composition as defined by claim 1:
(i) devoid of any octyl methoxycinnamate; and
(ii) being other than a solution of butyl methoxydibenzoylmethane in 2-phenylethyl benzoate, 2-phenylethyl o-toluate, 2-phenylethyl p-toluate or in a 2-phenylethyl o-toluate/2-phenylethyl p-toluate (1/1) mixture.

6. The cosmetic/dermatological composition as defined by claim 1, said at least one arylalkyl benzoate compound comprising from 0.1 to 40% by weight thereof.

7. The cosmetic/dermatological composition as defined by claim 1, said at least one dibenzoylmethane UV-screening agent comprising from 0.01 to 10% by weight thereof.

8. The cosmetic/dermatological composition as defined by claim 1, further comprising at least one other UV-A active and/or UV-B active organic or mineral photoprotective agent that is water-soluble or liposoluble or insoluble in the cosmetic solvents commonly employed.

9. The cosmetic/dermatological composition as defined by claim 8, comprising at least one additional organic photoprotective agent selected from among anthranilates; salicylic derivatives, camphor derivatives; benzophenone derivatives; β,β-diphenylacrylate derivatives; benzotriazole derivatives; benzalmalonate derivatives; benzimidazole derivatives; imidazolines; bis-benzoazolyl derivatives; p-aminobenzoic acid (PABA) derivatives; methylenebis-(hydroxyphenylbenzotriazole) derivatives; benzoxazole derivatives; screening polymers and screening silicones; dimers derived from α-alkylstyrene; 4,4-diarylbutadienes, and mixtures thereof.

10. The cosmetic/dermatological composition as defined by claim 9, comprising at least one organic UV-screening agent selected from among the following compounds:

Ethylbexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenodicamphorsulfonic acid,
Disodium phenyl dibenzimidazole tetrasulfonate,
Methylenebis(benzotriazolyl)tetramethylbutylphenol,
Ethylhexyl triazone,
Diethylhexyl butamido triazone,
Drometrizole trisiloxane,
Polysilicone-15,
1,1-Dicarboxy(2,2'-dimethylpropyl)-4,4-diphenylbutadiene,
2,4-bis[5-(1-Dimelhylpropyl)benzoxazol-2-yl-(4-pheny9imino]6-(2-ethylhexyl)imino-1,3,5-triazine,
and mixtures thereof.

11. The cosmetic/dermatological composition as defined by claim 8, comprising at least one additional mineral photoprotective agent which comprises treated or untreated metal oxide pigments or nanopigments.

12. The cosmetic/dermatological composition as delined by claim 11, comprising pigments or nanopigments selected from among titanium oxide, zinc oxide, iron oxide, zirconium oxide and cerium oxide, and mixtures thereof, which are treated or untreated.

13. The cosmetic/dermatological composition as defined by claim 1, further comprising at least one agent for artificially tanning and/or browning the skin.

14. The cosmetic/dermatological composition as defined by claim 1, further comprising at least one adjuvant selected from among fatty substances, organic solvents, ionic or nonionic, hydrophilic or lipophilic thickeners, softeners, humectants, opacifiers, stabilizers, emollients, silicones, antifoaming agents, fragrances, preservatives, anionic, cationic, nonionic, zwitterionic or amphoteric surfactants, active agents, fillers, polymers, propellants, and acidifying or basifying agents.

15. A regime or regimen for cosmetically treating or caring for the skin, lips, nails, hair, eyelashes, eyebrows and/or scalp of an individual in need of such treatment, comprising topically applying thereon, a thus effective amount of the cosmetic/dermatological composition as defined by claim 1.

16. A regime or regimen for photoprotecting the skin, hair, lips and/or scalp against the damaging effects of UV-irradiation, comprising topically applying thereon, a thus effective amount of the cosmetic/dermatological composition as defined by claim 1.

17. A process for enhancing the stability with respect to UV-irradiation of at least one dibenzoylmethane UV-screening agent, comprising formulating therewith a thus effective amount of at least one arylalkyl benzoate compound.

18. The cosmetic/dermatological composition as defined by claim 1, formulated as an emulsion, a milk, a gel, a cream, a lotion, a powder, a stick, a mousse, or a spray.

* * * * *